United States Patent
Procureur et al.

(10) Patent No.: US 9,528,970 B2
(45) Date of Patent: Dec. 27, 2016

(54) MULTIPLEXED CONNECTION CIRCUIT AND DEVICE FOR DETECTING AT LEAST ONE PARTICLE USING THE CONNECTION CIRCUIT

(71) Applicant: Commissariat a L'energie Atomique et aux Energies Alternatives, Paris (FR)

(72) Inventors: Sebastien Procureur, Palaiseau (FR); Stefan Aune, Palaiseau (FR); Raphael Dupre, Massy (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 426 days.

(21) Appl. No.: 14/140,872

(22) Filed: Dec. 26, 2013

(65) Prior Publication Data

US 2014/0188408 A1   Jul. 3, 2014

(30) Foreign Application Priority Data

Dec. 27, 2012   (FR) ...................................... 12 62815

(51) Int. Cl.
  *G01F 17/00*   (2006.01)
  *G01N 33/00*   (2006.01)
  *G01T 1/17*   (2006.01)

(52) U.S. Cl.
  CPC ............ *G01N 33/0022* (2013.01); *G01T 1/17* (2013.01)

(58) Field of Classification Search
  CPC ............ G01T 1/166; G01T 1/164; G01T 1/20; G01T 1/17; G01N 33/0022
  See application file for complete search history.

(56) References Cited

U.S. PATENT DOCUMENTS

2007/0114423 A1*   5/2007   Vester .................. G01T 1/1644
                                                              250/369

FOREIGN PATENT DOCUMENTS

DE   10 2005 055656 B3   1/2007

OTHER PUBLICATIONS

Search report issued by French Patent Office for priority French application FR 1262815 dated Aug. 22, 2013.
(Continued)

*Primary Examiner* — Matthew G Marini
(74) *Attorney, Agent, or Firm* — Frommer Lawrence & Haug LLP (57) ABSTRACT

The multiplexed connection circuit (100) comprises a plurality of channels furnished with p channels (101), in particular configured so as to detect at least one particle, and a plurality of output pathways furnished with n output pathways (102), with p>n, each channel being connected to a lone output pathway (102). The circuit furthermore comprises groups of adjacent channels, each channel (101) of the connection circuit (100) belonging to at least one group of adjacent channels and each group of adjacent channels being defined by an assembly formed by the connections of the channels (101) of the group of adjacent channels to the corresponding output pathways (102), this assembly forming a group of output pathways which is associated with the group of adjacent channels, and each group of adjacent channels is associated with a single group of output pathways, different from that of the other groups of adjacent channels.

13 Claims, 2 Drawing Sheets

(56) References Cited

OTHER PUBLICATIONS

Lee, Lap Yen et al.: "Multi-Strip Scintillation Counters (MSSC)", *Nuclear Instruments and Methods*, 119, (1974), pp. 29-33.
Crow, M.L. et al.: "Shifting scintillator prototype large pixel wavelength-shifting fiber detector for the POWGEN3 powder diffractometer",*Nuclear Instruments and Methods in Physics Research A*, 529 (2004), pp. 287-292.

* cited by examiner

MULTIPLEXED CONNECTION CIRCUIT AND DEVICE FOR DETECTING AT LEAST ONE PARTICLE USING THE CONNECTION CIRCUIT

TECHNICAL FIELD OF THE INVENTION

The invention relates to the field of connection circuits making it possible in particular to carry out multiplexing.

The subject of the invention is more especially a multiplexed connection circuit and a device for detecting and in particular for locating at least one particle comprising the said connection circuit.

PRIOR ART

Gaseous detectors based on tracks or micro-tracks are used in numerous fields, and more especially in particle physics and in medical imaging to locate particles. They require the installation of a large number of output pathways (up to several tens or indeed hundreds of thousands), also called electron pathways or electronic pathways in the field. The total cost of these output pathways is often much greater than that of manufacturing the detection elements. In order to limit the costs of manufacturing such detectors, a need has resulted to find solutions for decreasing the number of output pathways.

With a view to satisfying this need, a solution has been proposed which makes it possible to locate a particle at the level of a location device implementing a connection circuit with a specific multiplexing.

Figure 1:
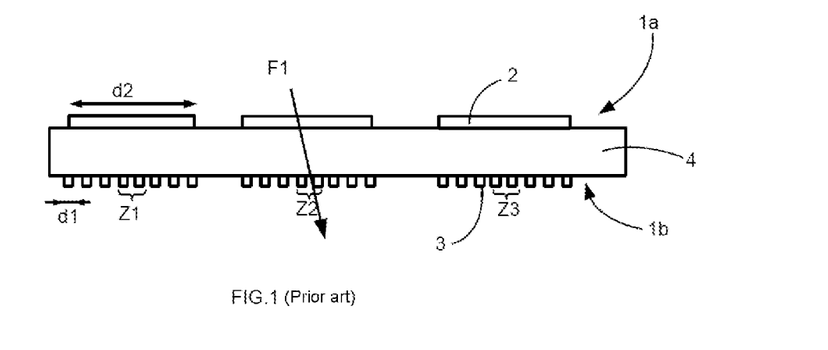
FIG. 1 is a side view of a location device according to the prior art.

Such a multiplexing solution has consisted in the development of a particle location device termed "double-face". As illustrated in FIG. 1, a first face 1a of the location device comprises i big tracks 2 (i being equal to 3 in the example illustrated), and a second face 1b of the location device comprises p little tracks 3 (p being equal to 8 in the example) which repeat i times to form identical blocks under the big tracks 2. The two faces 1a and 1b are, in the example, delimited by a printed circuit 4. Passage F1 of a particle through the two faces 1a, 1b of the location device allows location of the said particle with a precision corresponding to the spacing of the little tracks 3. In fact, the little tracks 3 being multiplexed, a big track 2 allows first location in an assembly of little tracks 3, and location at the level of one or more little tracks 3 opposite an associated big track 2 makes it possible to locate the particle precisely.

The difference between "little" and "big" corresponds to the fact that a little track exhibits a smaller lateral dimension d1 than the lateral dimension d2 of a big track.

In fact, without the big tracks 2, the passage of the particle would generate an item of data which, because of the multiplexing, would be regarded as a location in a zone Z1, a zone Z2 or a zone Z3 of the location device. The multiplexing illustrated in FIG. 2 allows better understanding of the problem involved, indeed, the particle received along F1 is received by the two tracks 3a, 3b surrounding the tip of the arrow F1. This particle will therefore be associated with output pathways V4 and V5 which are also associated with other tracks of the assembly of little tracks, hence the benefit of producing a filter with the big tracks 2 of FIG. 1.

Figure 2:
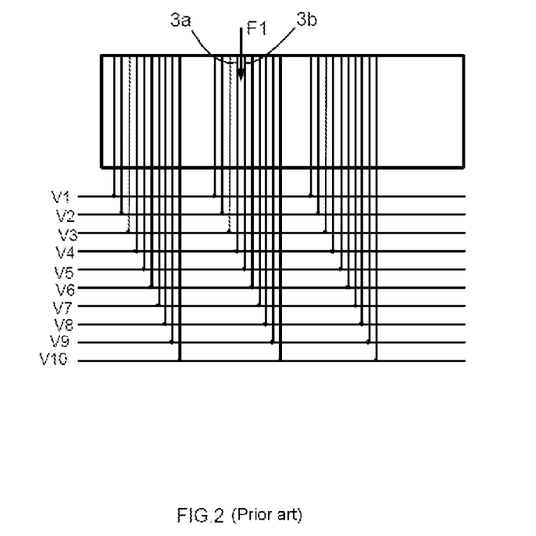
FIG. 2 is a view from below of the location device of FIG. 1.

The type of multiplexing illustrated in FIGS. 1 and 2 makes it possible with the aid of a circuit with i+p tracks to produce an equivalent detector with i*p tracks.

However, such a solution presents various drawbacks, including in particular:

difficulty of manufacture since it is in fact necessary to manufacture two detection assemblies on either side of the printed circuit, the use of a large amount of material: the printed circuit on which the tracks are formed must be sufficiently rigid and therefore thick. This is often a handicap in detection, where the amount of material must be minimized.

unsuitability for large fluxes of particles: if several particles pass through the location device simultaneously, it is no longer possible to locate these particles precisely, thereby leading to ineffectiveness of detection, the setting defaults of the location if the angle of the incident particle is too large: indeed, the particle may then leave a signal on a big track and on the little tracks opposite a neighbouring big track, thereby leading to ambiguity of location, in particular as a function of the thickness of the printed circuit 4 between the two faces 1a, 1b, finally the degree of multiplexing is not optimal, indeed, if there are in total n output pathways, the location device can be equipped with up to $n^2/4$ tracks with $i=p=n/2$.

OBJECT OF THE INVENTION

The aim of the present invention is to propose a solution which remedies at least in part the drawbacks listed hereinabove.

This aim is addressed by virtue of a multiplexed connection circuit comprising a plurality of channels furnished with p channels, in particular configured so as to detect at least one particle, and a plurality of output pathways furnished with n output pathways, with p>n, each channel being connected to a lone output pathway, the said circuit comprising groups of adjacent channels, each channel of the connection circuit belonging to at least one group of adjacent channels and each group of adjacent channels being defined by an assembly formed by the connections of the channels of the group of adjacent channels to the corresponding output pathways, this assembly forming a group of output pathways which is associated with the group of adjacent channels, and each group of adjacent channels is associated with a single group of output pathways, different from that of the other groups of adjacent channels.

Preferably, the circuit comprises connection points between the channels and the output pathways making it possible to carry out the connection of each channel of the plurality of channels to a lone output pathway of the plurality of output pathways, and the connection points:

define the groups of adjacent channels, form the groups of output pathways, the said output pathways of each of the groups of output pathways being chosen from among the n output pathways of the plurality of output pathways without the order of the output pathway in the group of output pathways having any importance and so that the groups of output pathways are all different from one another, a group of output pathways and an associated group of channels comprising respectively a number of output pathways and a number of channels which are equal.

Advantageously, at least one of the output pathways of the plurality of output pathways is connected to at least two channels of the plurality of channels of two groups of distinct channels.

Preferably, each group of channels comprises k channels and each group of output pathways comprises k output pathways with k≥2. For example, k being equal to 2, the connections are carried out so that the plurality of channels comprises immaterially between 2 and $$\frac{n*(n-1)}{2}+1$$

channels.

Advantageously, the circuit comprises z unordered different groups of output pathways with z any integer number chosen immaterially between 2 and $C_n^k$. For example p=z+k−1.

According to one embodiment, two channels belonging to two groups of different channels and linked to one and the same output pathway are separated by at least x distinct channels, in particular with x greater than the number of channels of each group of channels.

Preferably, the plurality of channels is arranged in such a way that each of the channels of the plurality of channels is adjacent to at least one, and preferably substantially parallel, other channel of the plurality of channels.

If the channels are tracks, each of the tracks is at the maximum adjacent to two other tracks.

The invention also relates to a device for detecting at least one particle comprising at least one connection circuit such as described, each of the channels of the plurality of channels of which forms a particle detection channel, and this device comprises:
- a detection element intended to receive the said at least one particle to be located and comprising the plurality of detection channels so that a particle is detected by the propagation of a detection signal in at least two adjacent detection channels, and
- an analysis component linked to each of the output pathways of the plurality of output pathways.

Preferably, the device is configured so that the said particle to be located is detected by at least all the channels of one of the groups of adjacent detection channels, and that the detected particle is located, by the analysis component, in a lone zone of the detection element solely on the basis of detection data arising from the detection channels having detected the said particle and transmitted to the said analysis component by the output pathways of the group of output pathways which is associated with the group of channels that has detected the said particle.

The invention also relates to a method for locating at least one particle on the basis of a detection device such as described, the method comprising:
- a step in which the said at least one particle is received by the detection element,
- a step of detection by at least all the detection channels of one and the same group of adjacent channels of the said at least one particle,
- a step of generating detection data by each of the detection channels of the group of adjacent detection channels that has detected the said at least one particle,
- a step of reception by the analysis component of the said detection data transmitted by the output pathways connected to the said group of adjacent detection channels that has detected the said at least one particle,
- a step of determination, on the basis of the said detection data received, of an associated group of output pathways,
- a step of determining a zone of the detection element comprising the group of adjacent detection channels which is connected to the determined group of output pathways, the said zone of the detection element providing an item of data regarding location of the said at least one particle.

The invention also relates to a data recording medium readable by a computer, on which is recorded a computer program comprising computer program code means for implementing the steps of a location method such as described.

The invention also relates to a computer program comprising a computer program code means suitable for carrying out the steps of a location method such as described, when the program is executed by a computer.

SUMMARY DESCRIPTION OF THE DRAWINGS

Other advantages and characteristics will emerge more clearly from the description which follows of particular embodiments of the invention, given by way of nonlimiting examples and represented in the appended drawings, in which.

DESCRIPTION OF PREFERENTIAL MODES OF THE INVENTION

Figure 3:
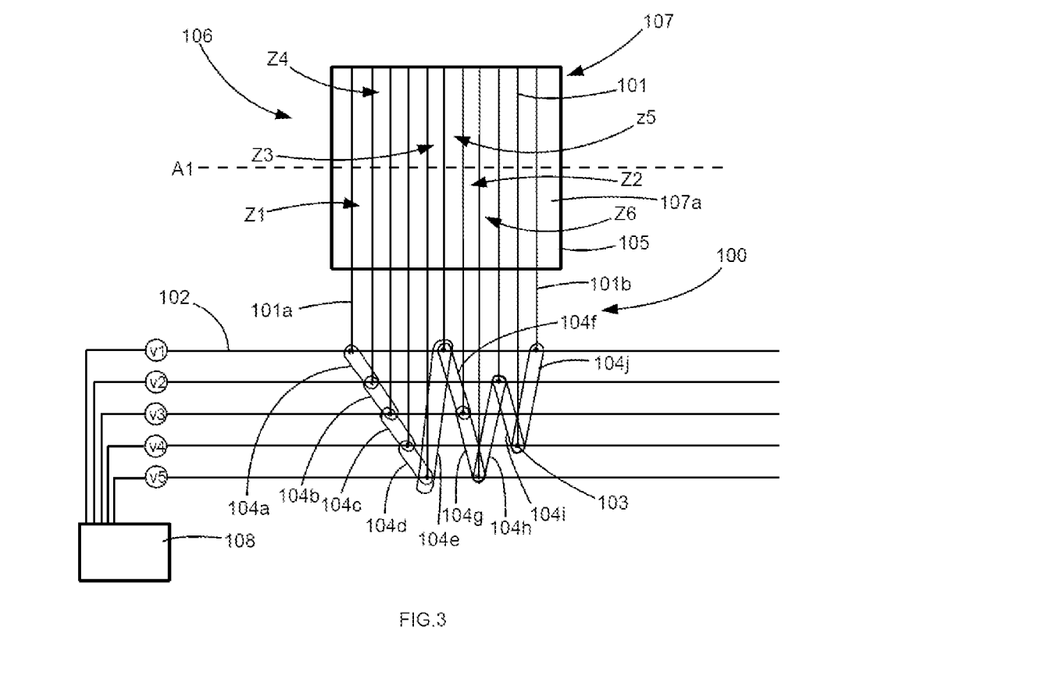
FIG. 3 illustrates a view of a detection device according to a mode of execution of the invention.

In FIG. 3, the multiplexed connection circuit 100, in particular for a device for detecting at least one particle (making it possible in particular to locate the said at least one particle), comprises a plurality of channels furnished with p channels 101, in particular configured so as to detect at least one particle, and a plurality of output pathways furnished with n output pathways 102, with p>n.

Each channel is connected to a lone output pathway 102. The circuit 100 comprises groups of adjacent channels and each channel 101 of the connection circuit 100 belongs to at least one group of adjacent channels. Each group of adjacent channels is defined by an assembly (in the present description "assembly" can also be replaced by the word "set") formed by the connections of the channels 101 of the group of channels adjacent to the corresponding output pathways 102. This assembly forms a group of output pathways which is associated with the group of adjacent channels and each group of adjacent channels is associated with a single group of output pathways, different from that of the other groups of adjacent channels.

This type of multiplexing makes it possible in particular to multiplex more channels for one and the same number of pathways, as compared with the prior art. This multiplexing is especially suited to detection devices where the passage of a particle generates a signal propagated in at least two adjacent channels. It is on the basis of this propagation that detection is considered to have taken place and accordingly, therefore, the channels can be configured so as to detect at least one particle.

The connection circuit furthermore comprises connection points 103 (represented by black dots in FIG. 3 at the level of each junction of a channel connected to an output pathway) between the channels 101 and the output pathways

102 making it possible to carry out the connection of each channel of the plurality of channels to a lone output pathway 102 of the plurality of output pathways.

In the present description, an output pathway (or electron pathway, or else electronic pathway) is configured so as to allow through an item of data, for example an electrical signal or the like. To generalize, the connection points 103 are configured so as to allow, if appropriate, an item of data to pass from a channel to a pathway at the level of the connection point 103 between the said channel and the said pathway, this item of data being able to be altered or modified type-wise (electrical, optical, etc.) during passage. The connection points can be of electrical type, the channels and the pathways are then electrically conducting for example in track or pixel form, or else of optical type, the channels and the pathways then being configured so as to form waveguides, or else of mechanical type: the channels and the pathways then being mechanical transmissions.

Moreover, according to an implementation, the connection points 103 are such that they define the groups of adjacent channels, in particular the said adjacent channels 101 of each of the groups of channels are chosen from among the plurality of channels, and that they form the groups of output pathways, the said output pathways 102 of each of the groups of output pathways preferably being chosen from among the n output pathways 102 of the plurality of output pathways without the order of the pathway in the output pathway group having any importance and so that the groups of output pathways are all different from one another. It is understood that a group of output pathways and a group of associated channels comprise respectively a number of output pathways and a number of channels which are equal. Stated otherwise, the connection points 103 can be such that they associate each group of output pathways with a single of the groups of adjacent channels and conversely, each group of output pathways comprising a number of pathways which is equal to the number of channels of the associated group of channels.

For example, in a group of adjacent channels, the channels constituting this group are in fact adjacent to two or to several other channels of this group.

Preferably, all the output pathways of the plurality of output pathways belong to at least one group of output pathways.

As mentioned previously, all the channels of the plurality of channels (that is to say of the connection circuit) belong to at least one group of channels. In the case where the number of channels and the number of output pathways in their respective groups is equal to two, all the channels, with the exception optionally of two end channels, of the plurality of channels can each be associated with two groups of output pathways.

Stated otherwise, the groups of output pathways are all different, but certain groups of output pathways can have at least one output pathway in common. If the groups of output pathways each have the same number of output pathways, the maximum number of groups of output pathways is defined mathematically by the combinations of k from among n, with k the number of output pathways per group, i.e.

$$C_n^k = \frac{n!}{k!(n-k)!}.$$

In the particular example of FIG. 3, each group of output pathways is in fact a pair. Starting on the basis of five available pathways V1, V2, V3, V4, V5, it is known that it is possible to have at most ten distinct groups 104a, 104b, 104c, 104d, 104e, 104f, 104g, 104h, 104i, 104j, formed respectively by (V1; V2), (V2; V3), (V3; V4), (V4; V5) (V5; V1), (V1; V3), (V3; V5), (V5; V2), (V2; V4) and (V4; V1). These groups of output pathways make it possible to multiplex 11 channels by forming 10 pairs of adjacent channels. Thus, the connection circuit can comprise p-1 pairs of adjacent channels and $C_n^2$ different pairs of output pathways such as defined previously, and each pair of adjacent channels being associated with a distinct pair of output pathways and vice versa. Apart from the two groups of channels comprising the end channels 101a and 101b, the two channels of each group of channels each belong to another group of channels.

According to a variant, each channel belongs to a lone group of adjacent channels.

Preferably, to improve the multiplexing and to decrease the number of necessary output pathways, each (or at least one) of the output pathways 102 of the plurality of output pathways is connected to at least two channels 101 of the plurality of channels of two groups of distinct channels.

According to a mode of execution, each group of channels comprises k channels and each group of output pathways comprises k output pathways with k≥2. Stated otherwise, the number of output pathways of each group of output pathways is equal to the number of channels of each group of channels.

In fact, if k is equal to 2, the connections 103 are carried out so that the plurality of channels comprises immaterially (indifferently) between 2 and $$\frac{n*(n-1)}{2}+1$$

channels (stated otherwise, $$2 \leq p \leq \frac{n*(n-1)}{2}+1).$$

It is therefore possible to form on the basis of such a connection circuit an equivalent particle detection device comprising up to $$\frac{n*(n-1)}{2}+1$$

channels by using a construction such as that indicated hereinabove.

Stated otherwise, for n pathways numbered from V1 to Vn, it is for example possible to make connections with the 1$^{st}$ available output pathway V1 and in this case:

One begins by connecting in order individually the first n channels to the n output pathways V1 to Vn (This merely being a numbering convention), Next the n+1$^{th}$ channel is again connected to the 1$^{st}$ output pathway V1, the n+2$^{th}$ channel cannot be connected to the 2$^{nd}$ output pathway, since then the group of pathways V1-V2 would be present twice. On the other hand, it is possible to connect this n+2$^{th}$ channel to the 3$^{rd}$ output pathway, since the doublet V1-V3 is not yet used.

The procedure is continued identically: if channel i of the detector is connected to output pathway j, then one connects channel i+1 to the first available output pathway h after pathway j. Available signifies that the doublet j-h (or h-j since the groups of pathways are not ordered) does not yet appear in the connection circuit.

This procedure makes it possible to construct (n-1)/2 series of the n output pathways. It is optionally possible to require that each series contain each electronic pathway exactly once. In a particular example where n equals 15, the following list indicates to which pathways the successive channels are connected:

V1-V2-V3-V4-V5-V6-V7-V8-V9-V10-V11-V12-V13-V14-V15 (1$^{st}$ series of n channels)

V1-V3-V5-V7-V9-V11-V13-V15-V2-V4-V6-V8-V10-V12-V14 (2$^{nd}$ series of n channels)

V1-V4-V7-V10-V13-V2-V5-V8-V11-V14-V3-V6-V9-V12-V15 (3$^{rd}$ series of n channels)

V3-V7-V11-V15-V4-V8-V12-V1-V5-V9-V13-V6-V10-V14-V2 (4$^{th}$ series of n channels)

V6-V11-V1-V7-V12-V2-V8-V13-V3-V9-V14-V4-V10-V15-V5 (5$^{th}$ series of n channels)

V10-V1-V6-V12-V3-V8-V14-V5-V11-V2-V7-V13-V4-V9-V15 (6$^{th}$ series of n channels)

V6-V14-V7-V15-V8-V1-V9-V2-V10-V3-V11-V4-V12-V5-V13 (7$^{th}$ series of n channels)

In this particular case, 15 pathways make it possible to connect 105 channels. According to this example it is clearly seen that each doublet i-j appears just once in the said list.

According to another procedure, in the r$^{th}$ series of channels, the first channel is connected to the 1$^{st}$ available electronic pathway, and then we go r by r, modulo n. This procedure makes it possible to construct all the doublets very easily if n is a prime number. This procedure is illustrated hereinbelow with n=11 and gives the list:

V1-V2-V3-V4-V5-V6-V7-V8-V9-V10-V11 (1$^{st}$ series, connections 1 by 1)

V1-V3-V5-V7-V9-V11-V2-V4-V6-V8-V10 (2$^{nd}$ series, connections 2 by 2)

V1-V4-V7-V10-V2-V5-V8-V11-V3-V6-V9 (3$^{rd}$ series, connections 3 by 3)

V1-V5-V9-V2-V6-V10-V3-V7-V11-V4-V8 (4$^{th}$ series, connections 4 by 4)

V1-V6-V11-V5-V10-V4-V9-V3-V8-V2-V7 (5$^{th}$ series, connections 5 by 5)

Here again, it may be verified that each doublet i-j appears just once in the list.

However, if all the possible pairs/doublets such as envisaged hereinabove are used and if two particles pass through a detection device equipped with such a connection circuit simultaneously, a location ambiguity may possibly appear, in this case it no longer becomes possible to locate the particles precisely. For example, if two particles are actually received at the level of zones Z1 and Z2 (FIG. 3), they leave respectively a signal on the pathways V1, V2, V3, and V5, three location solutions are then possible: (V1; V2); (V3; V5) or (V1; V5); (V3; V2) or (V1; V3); (V2; V5) corresponding respectively to the zones Z1 and Z2, or to the zones Z3, Z4, or to the zones Z5 and Z6. In this particular case, it is not possible to say which solution is the right one, since all these groups of output pathways appear in the detection device. On the other hand, it is easy to remove part of the groups of output pathways during manufacture of the circuit, in particular of the connections of the circuit, thereby making it possible to resolve ambiguities when several particles pass through the detector simultaneously. Stated otherwise, within the context of a particle detection device (making it possible in particular to locate one or more particles) equipped with such a connection circuit, the connection points 103 of the connection circuit are such that only a fraction of the groups of output pathways is formed so that when two particles are received in any zone whatsoever of a detection element associated with the said plurality of channels, they are located by decreasing the possibilities of ambiguity. Of course, this removing of some of the doublets is done to the detriment of the number of output pathways.

Returning to a slightly more general case and considering that the number of output pathways of each group of output pathways is equal to the number of channels of each group of channels, the circuit can comprise z unordered different groups of output pathways with z any integer number chosen immaterially between 2 and $C_n^k$ (stated otherwise $2 \leq z \leq C_n^k$).

Preferably, p is equal to z+k−1. This particular case allows the greatest saving in output pathways.

According to an implementation, two channels belonging to two groups of different channels and linked to one and the same output pathway are separated by at least x distinct channels, in particular with x greater than a maximum number of channels having detected a particle within the context of a particle detection/location device (stated otherwise, x is greater than the number of channels of each group of channels). This allows maximum separation of two channels connected to the same output pathway, in particular so as to avoid ambiguous location when the connection circuit is used within the context of a particle detection device.

Figure 4:
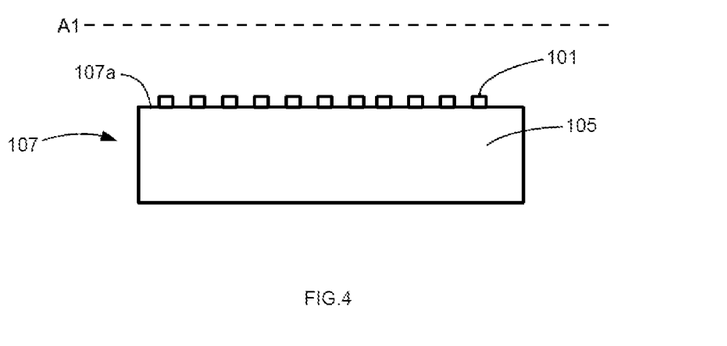
FIG. 4 illustrates a side view of the detection device of FIG. 3.

Preferably, the plurality of channels is arranged in such a way that each of the channels of the plurality of channels is adjacent to at least one other channel of the plurality of channels and in the case of tracks (that is to say that the channels are in fact tracks), at the maximum adjacent to two other tracks of the plurality of tracks. Preferably, the channels are substantially parallel to one another. Stated otherwise, the channels of the plurality of channels can be disposed side by side and staggered along the axis A1 of FIGS. 3 and 4 (preferably the channels are substantially perpendicular to the axis A1). The channels can be disposed on one and the same face of one and the same support substrate 105. The support substrate is able to be functionalized or not. For example, the support substrate 105 is a printed circuit.

Another subject of the invention is a detection device 106 (FIG. 3) for detecting at least one particle. Such a detection device comprises at least one connection circuit 100 such as described previously, each of the channels 101 of the plurality of channels of which forms a particle detection channel (it being possible for the particle to be considered to be detected when a signal propagates in one or more channels). Stated otherwise, a particle can be considered to be detected when it is received by the said device at the level of the detection channel considered.

In fact, the phraseology channels for particle detection or configured so as to detect at least one particle is understood to mean a channel able to recover a signal for example generated in a detection medium when the said particle reaches the detection medium. For example, if the particle interacts in the detection medium, the latter may generate, on the basis of the particle, either charges or photons which are recovered by the channel or channels so as to constitute a signal of interest to be analysed in order to locate the particle thus detected. This recovery is generally done solely at the level of the site where the particle has interacted.

Furthermore, the detection device also advantageously comprises a detection element 107 intended to receive the said at least one particle to be located and this detection element comprises the plurality of detection channels so that a particle is detected by the propagation of a detection signal in at least two adjacent detection channels. The detection element 107 can then comprise the support substrate 105 such as defined hereinabove so that the detection channels extend over one and the same face 107*a* of the said support substrate 105 and are associated with a detection medium preferably covering the channels 101.

Moreover, the detection device comprises an analysis component 108 linked to each of the output pathways of the plurality of output pathways. This analysis component 108 makes it possible to locate a particle when the latter is detected by the detection element 107.

Preferably, the detection device 106 is configured so that the said particle to be located is detected by at least all the channels of one of the groups of adjacent detection channels (in particular by propagation of a detection signal in each of the channels of the said group of channels). This configuration is rendered possible by calibrating the spacing separating the adjacent channels and/or the dimensions of the adjacent channels as a function of the spatial extent of the signal generated by the particle or particles that it is sought to detect so that when a particle is received by the detection element, the signal impacts at least all the channels of one and the same group of channels. Thus, it is therefore beneficial to spread the signal so as to touch at least two channels. According to a variant, it is also possible to cover the channels by an element for spreading the signal making it possible to increase the number of channels receiving the signal, for example by using a spreading element in the form of a resistive paste or a resistive film in the case of an electrical connection circuit.

The phraseology "particle received" is understood to mean a particle which reaches the detection element 107 associated with the detection channels 101 of the plurality of channels. The particle possibly or possibly not pass through the detection element 107.

In the case where the particles do not arrive simultaneously, the detection device is also configured so that the detected particle is located, by the analysis component 108, in a lone zone of the detection element 107 solely on the basis of detection data arising from the detection channels 101 having detected (by propagation of the detection signal) the said particle. These detection data are transmitted to the said analysis component 108 by the output pathways 102 of the group of output pathways which is associated with the group of channels that has detected the said particle. In fact, according to a particular embodiment, the analysis component 108 comprises a location element associating with each detected particle a lone zone of the detection element 107, this association being determined on the basis of the detection data transmitted by the output pathways of the output pathway group associated with the group of channels that has detected the said particle.

The phraseology "lone zone" is understood to mean a lone assembly (or lone group) of adjacent channels of the detection element 107. This detection element 107 can then be divided into several distinct zones, and when a particle is received by the detection element it will subsequently be sought to locate it so as to know in which zone it was actually received.

In a more general manner and setting aside the connection circuit described hereinabove, the detection device can comprise a detection element intended to receive the particle to be located. The detection element also comprises a plurality of detection channels for example disposed on one and the same face of the detection element. The detection device comprises a plurality of output pathways, at least one of which is connected to at least two channels of the plurality of channels. Each of the channels of the plurality of channels is connected to a lone output pathway of the plurality of output pathways. Moreover, the detection device comprises an analysis component linked to each of the output pathways of the plurality of output pathways. The connections between the channels and the output pathways are such that the analysis component is configured so as to determine a single zone of location of the particle received by the detection element solely on the basis of data generated by the said detection channels of the plurality of detection channels and transmitted to the said analysis component by the output pathways associated with the detection channels having detected the said at least one particle. In fact, it is understood that, in contradistinction to the prior art, it is possible to detect and to locate a particle in a lone zone of the detection element without needing to equip the two opposite faces of the detection element with detection channels.

As mentioned previously, even if it is possible to carry out up to $$C_n^k = \frac{n!}{k!(n-k)!}$$

possible combinations of different and unordered groups of output pathways, it is possible to tailor the number of groups actually used in the detection device 106 so as to resolve ambiguities when several particles are received by the detection element simultaneously. In the particular case of triplets (groups of pathways of three pathways and groups of channels of three channels), it is not possible to construct a list containing all the possible triplets, but constructions similar to those presented previously succeed in forming a list of connections containing more than 75% of the possible triplets. Thus, with n=64, it is possible to construct a detection device 106 of more than 32000 detection channels, in which any triplet of pathways is present at most only once in the said detection device 106.

A method for locating at least one particle can be carried out on the basis of a detection device 106 such as described hereinabove in its various embodiments. Such a method can comprise: a step in which the said at least one particle is received by the detection element 107; a step of detection by at least all the detection channels 101 of one and the same group of adjacent channels of the said at least one particle (be this by direct detection or via the spreading element envisaged previously during the propagation of the detection signal on the basis of information arising from the detection medium); a step of generating detection data by each of the detection channels 101 of the group of adjacent detection channels that has detected the said at least one particle; a step of reception by the analysis component 108 of the said detection data transmitted by the output pathways 102 connected to the said group of adjacent detection channels that has detected the said at least one particle; a step of determination, on the basis of the said detection data received, of an associated group of output pathways; a step of determining a zone of the detection element comprising the group of adjacent detection channels which is connected to the determined group of output pathways, the said zone of the detection element providing an item of data regarding location of the said at least one particle. The zone of the detection element providing an item of data regarding location of the said at least one particle corresponds in fact to "the lone zone" described hereinabove. Preferably, the determined zone in which the particle is located can arise from a pre-established mapping associating a lone location zone with each group of output pathways.

A data recording medium readable by a computer, on which a computer program is recorded can comprise computer program code means for implementing the steps of the method such as described.

A computer program can comprise a computer program code means suitable for carrying out the steps of the method such as described when the program is executed by a computer.

Most, or indeed all, particle physics experiments could implement this kind of connection circuit with a view to detecting the said particles, with diverse degrees according to the flux of particles. There always exist zones where the flux of particles is lower, and where this principle could be successfully applied. Imaging could also exploit the multiplexing of the said connection circuit, in particular in muon tomography or in medical imaging. New experiments also become achievable, for example the construction of a detection assembly of very large area for studying cosmic radiation showers. Finally, the replacement of detectors of wire chamber type with detection devices based on micro-tracks (often prohibitive replacement because of the escalation in the number of pathways) becomes conceivable, with an appreciable improvement in positional resolution into the bargain.

In the present description, a detection device makes it possible in particular to locate one or more particles.

The invention claimed is:

1. Multiplexed connection circuit comprising a plurality of channels furnished with p channels, in particular configured so as to detect at least one particle, and a plurality of output pathways furnished with n output pathways, with p>n, each channel being connected to a lone output pathway, which comprises groups of adjacent channels, each channel of the connection circuit belonging to at least one group of adjacent channels and each group of adjacent channels being defined by an assembly formed by the connections of the channels of the group of adjacent channels to the corresponding output pathways, this assembly forming a group of output pathways which is associated with the group of adjacent channels, and in that each group of adjacent channels is associated with a single group of output pathways, different from that of the other groups of adjacent channels, wherein each group of channels comprises k channels and in that each group of output pathways comprises k output pathways with k≥2.

2. Connection circuit according to claim 1, wherein it comprises connection points between the channels and the output pathways making it possible to carry out the connection of each channel of the plurality of channels to a lone output pathway of the plurality of output pathways, and in that the connection points:
   define the groups of adjacent channels,
   form the groups of output pathways, the said output pathways of each of the groups of output pathways being chosen from among the n output pathways of the plurality of output pathways without the order of the output pathway in the group of output pathways having any importance and so that the groups of output pathways are all different from one another,
   a group of output pathways and an associated group of channels comprising respectively a number of output pathways and a number of channels which are equal.

3. Connection circuit according to claim 1, wherein at least one of the output pathways of the plurality of output pathways is connected to at least two channels of the plurality of channels of two groups of distinct channels.

4. Circuit according to claim 1, wherein it comprises z unordered different groups of output pathways with z any integer number chosen immaterially between 2 and $C_n^k$.

5. Connection circuit according to claim 4, wherein p=z+k−1.

6. Connection circuit according to claim 1, wherein the plurality of channels is arranged in such a way that each of the channels of the plurality of channels is adjacent to at least one, and preferably substantially parallel, other channel of the plurality of channels.

7. Connection circuit according to claim 6, wherein the channels are tracks, and in that each of the tracks is at the maximum adjacent to two other tracks.

8. Multiplexed connection circuit comprising a plurality of channels furnished with p channels, in particular configured so as to detect at least one particle, and a plurality of output pathways furnished with n output pathways, with p>n, each channel being connected to a lone output pathway, which comprises groups of adjacent channels, each channel of the connection circuit belonging to at least one group of adjacent channels and each group of adjacent channels being defined by an assembly formed by the connections of the channels of the group of adjacent channels to the corresponding output pathways, this assembly forming a group of output pathways which is associated with the group of adjacent channels, and in that each group of adjacent channels is associated with a single group of output pathways, different from that of the other groups of adjacent channels, wherein each group of channels comprises k channels, wherein k being equal to 2, the connections are carried out so that the plurality of channels comprises immaterially between 2 and $$\frac{n*(n-1)}{2}+1$$

channels.

9. Multiplexed connection circuit comprising a plurality of channels furnished with p channels, in particular configured so as to detect at least one particle, and a plurality of output pathways furnished with n output pathways, with p>n, each channel being connected to a lone output pathway, which comprises groups of adjacent channels, each channel of the connection circuit belonging to at least one group of adjacent channels and each group of adjacent channels being defined by an assembly formed by the connections of the channels of the group of adjacent channels to the corresponding output pathways, this assembly forming a group of output pathways which is associated with the group of adjacent channels, and in that each group of adjacent channels is associated with a single group of output pathways, different from that of the other groups of adjacent channels, wherein two channels belonging to two groups of different channels and linked to one and the same output pathway are separated by at least x distinct channels, in particular with x greater than the number of channels of each group of channels.

10. Device for detecting at least one particle, which comprises at least one connection circuit according to claim 1 of which each of the channels of the plurality of channels forms a particle detection channel, and in that it comprises:
   a detection element intended to receive the said at least one particle to be located and comprising the plurality of detection channels so that a particle is detected by the propagation of a detection signal in at least two adjacent detection channels, and
   an analysis component linked to each of the output pathways of the plurality of output pathways.

11. Device according to claim 10, wherein it is configured so that the said particle to be located is detected by at least all the channels of one of the groups of adjacent detection channels, and that the detected particle is located, by the analysis component, in a lone zone of the detection element solely on the basis of detection data arising from the detection channels (having detected the said particle and transmitted to the said analysis component by the output pathways of the group of output pathways which is associated with the group of channels that has detected the said particle.

12. Method for locating at least one particle on the basis of a device according to claims 10, wherein it comprises:
   a step in which the said at least one particle is received by the detection element,
   a step of detection by at least all the detection channels of one and the same group of adjacent channels of the said at least one particle,
   a step of generating detection data by each of the detection channels of the group of adjacent detection channels that has detected the said at least one particle,
   a step of reception by the analysis component of the said detection data transmitted by the output pathways connected to the said group of adjacent detection channels that has detected the said at least one particle,
   a step of determination, on the basis of the said detection data received, of an associated group of output pathways,
   a step of determining a zone of the detection element comprising the group of adjacent detection channels which is connected to the determined group of output pathways, the said zone of the detection element providing an item of data regarding location of the said at least one particle.

13. A non-transitory computer-readable medium storing program code that when executed by a processor carries out the steps of a method according to claim 12.

* * * * *